| (12) | United States Patent | (10) Patent No.: | US 6,455,257 B1 |
|---|---|---|---|
| | Fuerle | (45) Date of Patent: | Sep. 24, 2002 |

(54) DESIGNER DISEASES

(76) Inventor: Richard D. Fuerle, 1711 W. River Rd., Grand Island, NY (US) 14072

( * ) Notice: Subject to any disclaimer, the term of this patent is extended or adjusted under 35 U.S.C. 154(b) by 0 days.

(21) Appl. No.: 09/785,709

(22) Filed: Feb. 16, 2001

(51) Int. Cl.$^7$ .................................................. C12Q 1/68
(52) U.S. Cl. ........................ 435/6; 435/448; 435/285.1; 435/294.1; 435/297.1
(58) Field of Search ......................... 435/448, 6, 285.1, 435/294.1, 297.1

(56) References Cited

U.S. PATENT DOCUMENTS 5,871,464 A * 2/1999 Tryggvason et al. .......... 604/51

* cited by examiner

Primary Examiner—James Ketter
(74) Attorney, Agent, or Firm—Richard D. Fuerle

(57) ABSTRACT

An apparatus suitable for making a designer disease is disclosed. The apparatus comprises first, second, and third containers, each having two sections, I and II, separated by a semipermeable material through which a microbe can pass but cells from target and non-target populations cannot pass, and an entrance and an exit to each section. The entrance to section I of the first and second containers are circulation entrances, the exits from section II of the first and second containers are circulation exits, and the entrance to and exit from section I of the third container is a circulation entrance and a circulation exit, respectively. Conduits form a loop by connecting the circulation exit of each container to the circulation entrance to another container. A pump moves fluid around the loop and microbes in the fluid are mutated. A method of making a designer disease using that apparatus is also disclosed.

20 Claims, 1 Drawing Sheet

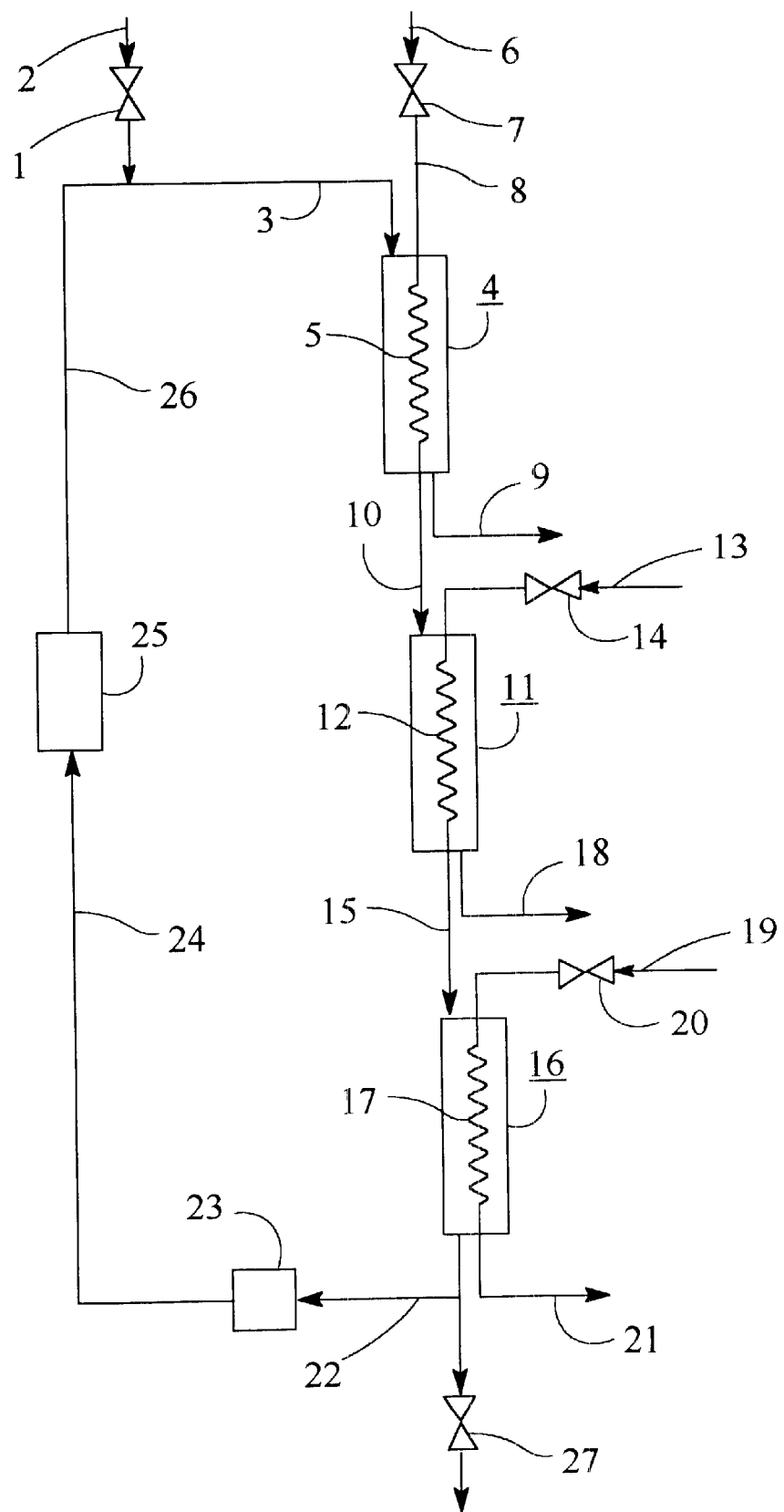

DESIGNER DISEASES

BACKGROUND OF THE INVENTION

This invention relates to a method and apparatus for making designer diseases. In particular, it relates to a method in which microbes are evolved to attack target cells but not non-target cells, and to an apparatus for performing that method.

Many plants, animals, and bacteria are undesirable or even dangerous, yet are difficult to destroy without injuring other nearby life forms. This is particularly true when the undesirable life form is closely related to the desirable life form. In that case, a biocide that attacks the undesirable life form may also kill, or at least harm, the closely related desirable life form.

A designer disease is a man-made disease that attacks particular life forms (targets) while being relatively innocuous towards other life forms (non-targets).

SUMMARY OF THE INVENTION

I have discovered a method and apparatus for making designer diseases. In this invention, microbes evolve until they attack cells of a target population, but do not attack cells of a non-target population, even when the non-target population is closely related to the target population. The method of this invention does not require complicated, expensive, or elaborate equipment.

BRIEF DESCRIPTION OF THE DRAWINGS

The accompanying drawing is a diagram illustrating a certain presently preferred embodiment of the apparatus of this invention.

DESCRIPTION OF THE PREFERRED EMBODIMENTS

In the drawing, valve 1 is opened and the microbe to be used is carried in fluid from line 2 through valve 1 into line 3 to the top of diffusor 4, which fills with microbe-containing fluid outside coil 5. Valve 1 is then closed. (After the initial charge of microbes, additional microbes should not be added to the system again.) Fluid, containing cells from the target population, enters line 6, passes valve 7, then goes through line 8 into coil 5. Coil 5 is made of a semipermeable material. The microbes can pass through the semipermeable material but the target cells cannot. Some of the microbes in diffusor 4 pass from the outside of coil 5 to the inside of coil 5. At this stage, microbes inside coil 5 may or may not attack the target cells inside coil 5. As the microbes move back and forth across the semipermeable material of coil 5, the microbes that attack target cells are more likely to be found inside coil 5 than outside coil 5. Microbes outside coil 5 are flushed out of diffusor 4 through line 9 as waste.

The mixture of target cells and microbes inside coil 5 passes though line 10 to diffusor 11 and fills diffusor 11 outside of coil 12, which is made of a semipermeable material. Fluid, without microbes or cells in it, is sent though line 13, pass valve 14, to the inside of coil 12. Microbes outside coil 12 pass to the inside of coil 12 and are sent through line 15 to diffusor 16, filling diffuser 16 outside of coil 17, which is made of a semipermeable material. The mixture of target cells, debris, and microbes outside coil 12 are flushed through line 18 to waste.

Fluid, containing cells from the non-target population, is sent through line 19, pass valve 20, to the inside of coil 17, then to waste in line 21. Some of the microbes outside coil 17 pass to the inside of coil 17. Some of the microbes inside coil 17 may attack non-target cells inside coil 17. Microbes inside coil 17 that do not attack non-target cells generally do not adhere to non-target cells and can pass back to the outside of coil 17 again. Microbes inside coil 17 that attack non-target cells enter the cells, or at least adhere to the cells, and are flushed out as waste in line 21. Microbes outside coil 17 pass through line 22 to pump 23, which pumps the fluid through line 24 to mutation station 25 where some of the microbes in the fluid are mutated. The fluid leaves mutation station 25 and passes though line 26 to line 3, forming a loop.

Thus, diffusor 4 gives the microbes an opportunity to attack target cells. Those that do go to diffusor 11 along with the target cells or pieces of target cells. Diffusor 11 separates the microbes that attacked the target cells from the target cells and other debris. Those microbes then go to diffusor 16, the purpose of which is to scavenge microbes that attack non-target cells. The microbes that leave diffusor 16 are those more likely to attack target cells and/or not attack non-target cells. In mutation station 25 the microbes are mutated, hopefully creating mutations that are even better at attacking target cells and/or not attacking non-target cells. The microbes are circulated and mutated repeatedly until they display the desired degree of abilities to attack target cells and not attack non-target cells. They can then be removed and collected by opening valve 27. It is also contemplated that the positions of diffusers 11 and 16 can be reversed, so that microbes that attack non-target cells are scavenged before the remaining microbes are separated from target cells and debris.

Diffusors 4, 11, and 16 are preferably made of transparent glass or plastic for observational purposes, but other materials, such as metal or ceramic, can also be used. Indeed, simple jars could suffice, though it is desirable that they be sealed to prevent other microbes from entering the system. Cylindrical diffusers are preferred, though other shapes can also be used. By placing diffusor 4 above diffusor 11 and diffusor 11 above diffusor 16, the fluid will flow under gravity so that it is possible to operate the apparatus using only a single pump.

Coils 5, 12, and 17 are made of a semipermeable material, that is, a material having openings therethrough that are large enough for the microbes to pass through but are too small for the cells to pass through. The coils are preferably made of a flexible polymeric membrane, but could also be made of porous ceramic, paper, or other suitable materials. An inexpensive coil could even be made by rolling up filter paper and sealing the edge with waterproof glue. To increase the transport of the microbes into and out of the coils, it is preferable to maximize the surface area of the coil and minimize the volume of fluid inside and outside the coils. While coils are preferred for their high surface area, other shapes can also be used.

The mutation station is preferably an ultraviolet light or a bank of ultraviolet lights as they are easy to use and effective. Mutation can also be accomplished by using chemical mutation agents, heat, radiation, or other means.

Target and non-target cells include plant cells, animal cells, and bacteria. Target cells will usually be selected from a population that is harmful to the non-target population. Examples of non-target and target populations include crops and weeds; birds and geckos on Guam and the brown tree snakes that prey on them; fish used for food and less desirable competing fish; humans and intestinal worms, amoebae, or bacteria; etc. The invention is particularly useful when the target and non-target cells are from the same species as it is difficult for other biocides to distinguish between sub-species. The type of target and non-target cells used are preferably those most likely to be attacked by the microbe. For example, if the target population is streptococci, the non-target population is children, and the microbe is a bacteriophage, human epithelial cells may be a good choice for the non-target cells.

The microbes are disease-causing agents that are smaller than the target and non-target cells so that they can pass through the semipermeable material but cells from the target and non-target populations cannot. The microbes can be prions, viruses, prokaryotes such as bacteria, and even small protozoa. While one can begin with a microbe that neither attacks the target population nor is harmless to the non-target population, it is preferable to select a microbe that occurs naturally in the same environment as the target population and either already attacks the target population, or at least life forms similar to the target population, or already is harmless to the non-target population. For example, to make a designer disease that will attack a weed, but not nearby crops, it would be preferable to select a microbe that already attacks the weed or a plant that is similar to the weed. The simplest microbes (e.g., viruses) are preferred to the more complex microbes as they evolve faster. It is preferable to use a mixture of genetically dissimilar microbes as that increases the probability of evolving a microbe that attacks target cells but not non-target cells. For example, if a particular virus is to be used, it is preferable to use a mixture of various strains of that virus.

The fluid used should be water-based and should not kill the target cells, the non-target cells, or the microbes. A saline solution can be used, for example, that contains the nutrients needed by the cells to live.

It will be necessary to adjust valve 7 so that the flow of target cell-containing fluid is slow enough to give the microbes time to attack and then get free of the target cells, yet fast to keep the process moving. If viruses are used, for example, the residence time of the target cells in diffusors 4 and 11 should be long enough for the viruses to enter the cells, reproduce, burst out of the cells, and pass into coil 12 before the contents of diffuser 11 are discarded. Valve 20 should be open enough so that there are always non-target cells available to be attacked inside coil 17. Valves (not shown) can also be placed on lines 9, 18, and 21 to control flow rates. If possible, fluid flows in the diffusors should be laminar and turbulence should be minimized. The percentage of the microbes in diffuser 4 that are discarded in line 9 for not attacking target cells and the percentage of microbes in diffusor 16 that are removed through line 21 are preferably high, about 90 to about 99.9%. Circulation time around the loop should initially be slow but can be increased as the microbes evolve to forms that more rapidly attack the target cells. A sample of the microbes can be taken and stored periodically so that the experiment can be restarted using the last sample should a catastrophic failure occur. In order to prevent the creation of microbes that are inferior in their ability to attack target cells without attacking non-target cells, mutation of the microbes should cease once the microbes have these abilities to the extent desired. Circulation through the loop should then be continued for a while to weed out any microbes still present in the apparatus that attack non-target cells.

I claim:

1. Apparatus for making a designer disease comprising
   (A) first, second, and third containers, each having two sections, I and II, separated by a semipermeable material through which a microbe can pass but cells from target and non-target populations cannot pass, and an entrance and an exit to each section, where the entrance to section I of said first and second containers is a circulation entrance, the exit from section II of said first and second containers is a circulation exit, and the entrance to and exit from section I of said third container is a circulation entrance and a circulation exit, respectively;
   (B) conduits forming a loop by connecting the circulation exit of each container to the circulation entrance of another container;
   (C) a pump for moving fluid around said loop; and
   (D) means for mutating microbes in said fluid.

2. Apparatus according to claim 1 wherein sections I are cylinders and sections II are tubes within said cylinders, and said tubes are made of said semipermeable material.

3. Apparatus according to claim 1 wherein the circulation exit of said first container is connected to the circulation entrance of said second container.

4. Apparatus according to claim 1 wherein the circulation exit of said first container is connected to the circulation entrance of said third container.

5. Apparatus according to claim 1 wherein said mutation station is at least one ultraviolet light.

6. Apparatus according to claim 1 wherein one of said containers is higher than the other two containers and one of the two lower containers is higher than the other of the two lower containers, so that said fluid flows by gravity from the highest container to the lowest container.

7. Apparatus according to claim 1 wherein said containers are transparent.

8. A method of making a designer disease using the apparatus of claim 1 comprising
   (A) passing cells from a target population in an aqueous fluid into the entrance to section II of said first container;
   (B) passing an aqueous fluid without microbes or cells in it into the entrance of section II of said second container;
   (C) passing cells from a non-target population in an aqueous fluid into the entrance of section II of said third container;
   (D) adding microbes to said loop;
   (E) circulating said aqueous fluid around said loop;
   (F) mutating some of the microbes in said loop; and
   (G) collecting microbes from said loop after they have an enhanced ability to attack cells from said target population or to not attack cells from said non-target population.

9. A method according to claim 8 wherein said aqueous fluid is a saline solution containing nutrients.

10. A method according to claim 8 wherein said microbes are viruses.

11. A method according to claim 8 wherein said microbes are bacteria.

12. A method according to claim 8 wherein said target population is the same species as said non-target population.

13. A method according to claim 8 wherein said target population and said non-target population are different species.

14. A method according to claim 8 wherein said means for mutating microbes is at least one ultraviolet light.

15. A method according to claim 8 wherein said non-target cells are human.

16. Apparatus for making a designer disease comprising
(A) first, second, and third diffusers, each comprising a cylinder having tube therein, where each tube is made of a semipermeable material through which microbes selected from the group consisting of viruses and prokaryotes can pass, but cells from target and non-target populations cannot pass, each cylinder and each tube having an entrance and an exit, where the entrance to the first and second cylinders are circulation entrances, the exit to the first and second tubes are circulation exits, and the entrance to and exit from the third tube is a circulation entrance and a circulation exit, respectively;
(B) conduits forming a loop by connecting the circulation exit of each diffuser to the circulation entrance of another diffuser;
(C) a pump for moving fluid around said loop; and
(D) means for exposing microbes in said fluid to mutating ultraviolet light.

17. A method of making a designer disease using the apparatus of claim 16 comprising
(A) passing cells from a target population in a saline solution into the entrance of the first tube;
(B) passing saline solution into the entrance of the second tube;
(C) passing cells from a non-target population in saline solution into the entrance of the third tube;
(D) injecting a charge of said microbes into said loop;
(E) discarding saline solution from the exits of the first and second cylinders and from the exit of the third tube;
(F) pumping said saline solution around said loop;
(G) exposing microbes in said loop to said ultraviolet light until they have evolved into microbes that are superior at attacking said target cells or at not attacking said non-target cells; and
(H) collecting said evolved microbes.

18. Apparatus for making a designer disease comprising
(A) first, second, and third diffusers, each comprising a transparent cylinder having an entrance and an exit, each cylinder containing a coil made of a semipermeable membrane through which viruses can pass but cells from target and non-target populations cannot pass, each coil having an entrance and an exit, where the entrance to the first and second cylinders are circulation entrances, the exits to the first and second coils are circulation exits, the entrance to and exit from the third coil is a circulation entrance and a circulation exit, respectively, and the exits from the first and second cylinders and from the third coil go to waste;
(B) conduits forming a loop by connecting the circulation exit of each diffuser to the circulation entrance of another diffuser;
(C) a pump for moving a saline solution around said loop; and
(D) at least one ultraviolet light positioned to mutate viruses in said saline solution.

19. A method of making a designer disease using the apparatus of claim 18 comprising
(A) passing cells from a target population in saline solution into the entrance of the first coil;
(B) passing saline solution into the entrance of the second coil;
(C) passing cells from a non-target population in saline solution into the entrance of the third coil;
(D) injecting a charge of viruses into said loop;
(E) pumping saline solution around said loop;
(F) discarding saline solution from the exits of the first and second cylinders and from the exit of the third coil;
(G) exposing viruses in said loop to said ultraviolet light until said viruses evolve into viruses that attack cells from said target population but do not attack cells from said non-target population;
(H) turning off said ultraviolet light;
(I) circulating saline solution around said loop to scavenge viruses that attack cells from said non-target population; and
(J) collecting viruses from said loop.

20. A method according to claim 19 wherein about 90 to about 99.9% of the viruses in said first and third diffusors are discarded in step (F).

* * * * *